(12) United States Patent
Leonov et al.

(10) Patent No.: US 6,441,216 B1
(45) Date of Patent: Aug. 27, 2002

(54) METHOD OF PREPARING LITHIUM COMPLEX SALTS FOR USE IN ELECTROCHEMICAL CELLS

(75) Inventors: Andrei Leonov; Armin de Meijere, both of Göttingen; Michael Schmidt, Weiterstadt, all of (DE)

(73) Assignee: Merck Patent Gesellschaft mit beschraenkter Haftung (DE)

( * ) Notice: Subject to any disclaimer, the term of this patent is extended or adjusted under 35 U.S.C. 154(b) by 46 days.

(21) Appl. No.: 09/613,293

(22) Filed: Jul. 10, 2000

(30) Foreign Application Priority Data

Jul. 10, 1999 (DE) .......................................... 199 32 317

(51) Int. Cl.⁷ .................................................. C07F 5/04
(52) U.S. Cl. ...................................... 558/291; 558/286
(58) Field of Search ................................ 558/286, 287, 558/288, 291; 429/188

(56) References Cited

PUBLICATIONS

US2001/0033964 A1 PG Publication by Heider et al Oct. 2001.*

CA:93:124874 abs of Z Anorg Allg Chem by Heller et al 460, pp. 228–234 1980.*

CA:128:180516 abs of DE 19633027 Feb. 1998.*

CA:131:47168 abs DE 1975126 Jun. 1999.*

* cited by examiner

Primary Examiner—Jean F. Vollano
(74) Attorney, Agent, or Firm—Millen, White, Zelano & Branigan, P.C.

(57) ABSTRACT

The invention relates to a method of preparing lithium complex salts and their intermediaries and to the use of these in electrolytes.

14 Claims, No Drawings

METHOD OF PREPARING LITHIUM COMPLEX SALTS FOR USE IN ELECTROCHEMICAL CELLS

The invention relates to a method of preparing lithium complex salts and to the use of these in electro-chemical cells.

Lithium ion batteries are amongst the most promising systems for mobile applications, the fields of application extending from sophisticated electronic appliances (e.g. mobile phones, camcorders) to batteries for electrically driven motor vehicles.

These batteries consist of cathode, anode, separator and a nonaqueous electrolyte. The cathodes used are typically $Li(MnMe_z)_2O_4$, $Li(CoMe_z)O_2$, $Li(CoNi_xMe_z)O_2$ or other lithium intercalation and insertion compounds. Anodes can consist of lithium metal, carbon materials, graphite, graphitic carbon materials or other lithium intercalation and insertion compounds or alloy compounds. The electrolyte used is in the form of solutions comprising lithium salts such as $LiPF_6$, $LiBF_4$, $LiClO_4$, $LiAsF_6$, $LiCF_3SO_3$, $LiN(CF_3SO_2)_2$ or $LiC(CF_3SO_2)_3$ and mixtures of these in aprotic solvents.

The standard conducting lithium salts have various drawbacks. Some conducting salts having low cycling yields (e.g. $LiBF_4$). Other conducting salts have low thermal stability (e.g. $LiPF_6$), and yet other conducting salts are not particularly suitable because of their toxicity and poor environmental safety (e.g. $LiAsF_6$).

WO 98/07729 therefore describes a novel class of conducting salts, the lithium borate complexes. These compounds gave particularly good results in cycling trials and proved especially stable. In combination with other salts, these complexes exhibit a synergistic stabilizing effect with respect to oxidation.

A description of lithium bis[5-fluoro-2-olato-benzenesulfonato(2)-O,O']borate(1−) reveals a conducting salt which, on the basis of its properties, must be regarded as a very promising conducting salt for use in lithium ion batteries. It does, however, present the problem of the cost-intensive and complicated synthesis of the precursors.

The only previous literature reference (Speier, The Preparation and Properties of (Hydroxyorgano)-silanes and related compounds, J. Am. Chem. Soc. 74 (1952), 1003) on the synthesis of 2-hydroxybenzenesulfonic acids and its derivatives describes this as a laborious three-step procedure with overall yields in the range of between 40 and 70%.

It is therefore a feature of the present invention to provide a simple method for the synthesis of lithium complex salts.

This feature is achieved by a method of preparing lithium complex salts of the general formula

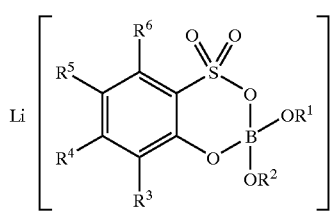

(I)

where $R^1$ and $R^2$ are identical or different, are directly linked or not directly linked to one another via a single or double bond, each, individually or jointly, have the meaning of an aromatic ring from the group phenyl, naphthyl, anthracenyl or phenanthrenyl, which can be unsubstituted or mono- to hexasubstituted by alkyl ($C_1$ to $C_6$), alkoxy groups ($C_1$ to $C_6$) or halogen (F, Cl, Br), or each, individually or jointly, have the meaning of an aromatic heterocyclic ring from the group pyridyl, pyrazyl or pyrimidyl, which can be unsubstituted or mono- to tetrasubstituted by alkyl ($C_1$ to $C_6$), alkoxyl ($C_1$ to $C_6$) or halogen (F, Cl, Br), or each, individually or jointly, have the meaning of an aromatic ring from the group hydroxybenzenecarboxyl, hydroxynaphthalenecarboxyl, hydroxybenzenesulfonyl and hydroxynaphthalenesulfonyl, which can be unsubstituted or mono- to tetrasubstituted by alkyl ($C_1$ to $C_6$), alkoxy groups ($C_1$ to $C_6$) or halogen (F, Cl, Br), $R^3$–$R^6$ can each, individually or pairwise, being directly linked or not directly linked to one another (i.e., are optionally directly linked to an adjacent ring substituent) via a single or double bond, have the following meaning:

1. alkyl ($C_1$ to $C_6$), alkyloxy ($C_1$ to $C_6$) or halogen (F, Cl, Br)
2. an aromatic ring from the groups phenyl, naphthyl, anthracenyl or phenanthrenyl, which can be unsubstituted or mono- to hexasubstituted by alkyl ($C_1$ to $C_6$), alkoxy groups ($C_1$ to $C_6$) or halogen (F, Cl, Br), pyridyl, pyrazyl or pyrimidyl, which can be unsubstituted or mono- to tetrasubstituted by alkyl ($C_1$ to $C_6$), alkoxyl ($C_1$ to $C_6$) or halogen (F, Cl, Br), characterized in that a) 3-, 4-, 5-, 6-substituted phenol (III) in a suitable solvent is admixed with chlorosulfonic acid, b) the intermediate (IV) from a) is reacted with chlorotrimethylsilane, and the product is filtered and subjected to fractional distillation, c) the intermediate (II) from b) is reacted with lithiumtetramethanolate borate(1−) in a suitable solvent and the end product (I) is isolated therefrom.

We have found that, starting from 3-, 4-, 5-, 6-substituted phenol (III), it is possible to prepare lithium complex salts in a 3-step synthesis. The starting material is a compound of the general formula:

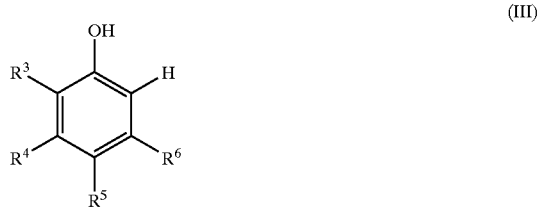

(III)

$R^3$–$R^6$ can each, individually or pairwise, being directly linked or not directly linked to one another via a single or double bond, have the following meaning:

1. alkyl ($C_1$ to $C_6$), alkyloxy ($C_1$ to $C_6$) or halogen (F, Cl, Br)
2. an aromatic ring from the groups phenyl, naphthyl, anthracenyl or phenanthrenyl, which can be unsubstituted or mono- to hexasubstituted by alkyl ($C_1$ to $C_6$), alkoxy groups ($C_1$ to $C_6$) or halogen (F, Cl, Br), pyridyl, pyrazyl or pyrimidyl, which can be unsubstituted or mono- to tetrasubstituted by alkyl ($C_1$ to $C_6$), alkoxy groups ($C_1$ to $C_6$) or halogen (F, Cl, Br).

The intermediate of the general formula (II):

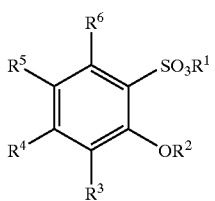
(II)

where $R^1$ and $R^2$ each, individually or jointly, have the following meanings:
$R^1$, $R^2$: H, alkyl having from 1 to 6 C atoms and trialkylsilyl (containing alkyl $C_1$ to $C_6$),
$R^3$–$R^6$ can each, individually or pairwise, being directly linked or not directly linked to one another via a single or double bond, have the following meaning:
1. alkyl ($C_1$ to $C_6$), alkyloxy ($C_1$ to $C_6$) or halogen (F, Cl, Br)
2. an aromatic ring from the groups
   phenyl, naphthyl, anthracenyl or phenanthrenyl, which can be unsubstituted or mono- to hexasubstituted by alkyl ($C_1$ to $C_6$), alkoxy groups ($C_1$ to $C_6$) or halogen (F, Cl, Br),
   pyridyl, pyrazyl or pyrimidyl, which can be unsubstituted or mono- to tetrasubstituted by alkyl ($C_1$ to $C_6$), alkoxy groups ($C_1$ to $C_6$) or halogen (F, Cl, Br),
can be synthesized in yields of between 80 and 90%.

The end product of the general formula (I) can be used in electrolytes of lithium batteries, either on its own on in combination with other lithium salts and/or borate complexes. In so doing it is important to make sure that the level of sodium-containing impurities is very low. Given the electrochemical properties (sodium is baser than lithium), sodium ions would otherwise be inserted into the structure of the negative electrodes. Ultimately this results in failure of the battery. The method according to the invention can dispense with the use of sodium.

Consequently, the lithium borate complexes prepared according to the invention are suitable in particular for use in electrochemical cells. The lithium borate complexes can be used, together with other lithium salts or alternatively with borate complexes, in electrolytes for secondary lithium batteries.

Alternatively, the lithium borate complexes can also be used in electrolytes comprising conventional conducting salts. Suitable, for example, are electrolytes comprising conducting salts selected from the group $LiPF_6$, $LiBF_4$, $LiClO_4$, $LiAsF_6$, $LiCF_3SO_3$, $LiN(CF_3SO_2)_2$ or $LiC(CF_3SO_2)_3$ and mixtures of these. The electrolytes may also comprise organic isocyanates (DE 199 44 603) to reduce the water content. Equally, the electrolytes can comprise organic alkali metal salts (DE 199 10 968) as an additive. A suitable example is that of alkali metal borates of the general formula $$Li^+B^-(OR^1)_m(OR^2)_p$$

where
m and p are 0, 1, 2, 3 or 4, with m+p=4, and $R^1$ and $R^2$ are identical or different,
are linked or not linked directly to one another via a single or double bond,
each, individually or jointly, have the meaning of an aromatic or aliphatic carboxylic, dicarboxylic or sulfonic acid radical, or
each, individually or jointly, have the meaning of an aromatic ring from the group phenyl, naphthyl, anthra-cenyl or phenanthrenyl which can be unsubstituted or mono- to tetrasubstituted by A or Hal, or
each, individually or jointly, have the meaning of a heterocyclic aromatic ring from the group pyridyl, pyrazyl or bipyridyl, which can be unsubstituted or mono- to trisubstituted by A or Hal, or
each, individually or jointly, have the meaning of an aromatic hydroxy acid from the group of aromatic hydroxy carboxylic acids or aromatic hydroxy sulfonic acids, which can be unsubstituted or mono- to tetrasubstituted by A or Hal,
and
Hal is F, Cl or Br
and
A is alkyl which has from 1 to 6 C atoms and can be mono- to trihalogenated. Equally suitable are alkali metal alcoholates of the general formula $$Li^+OR^-$$

where R
has the meaning of an aromatic or aliphatic carboxylic, dicarboxylic or sulfonic acid radical, or
has the meaning of an aromatic ring from the group phenyl, naphthyl, anthracenyl or phenanthrenyl which can be unsubstituted or mono- to tetrasubstituted by A or Hal, or
has the meaning of a heterocyclic aromatic ring from the group pyridyl, pyrazyl or bipyridyl, which can be unsubstituted or mono- to trisubstituted by A or Hal, or
has the meaning of an aromatic hydroxy acid from the group of aromatic hydroxy carboxylic acids or aromatic hydroxy sulfonic acids, which can be unsubstituted or mono- to tetrasubstituted by A or Hal,
and
Hal is F, Cl or Br
and
A is alkyl which has from 1 to 6 C atoms and can be mono- to trihalogenated.

Equally, the electrolytes can comprise compounds of the following formula (DE 199 41 566)

$$[([R^1(CR^2R^3)_k]_lA_x)_yKt]^+ \ {}^-N(CF_3)_2$$

where
Kt=N, P, As, Sb, S, Se
A=N, P, P(O), O, S, S(O), $SO_2$, As, As(O), Sb, Sb(O)
$R^1$, $R^2$ and $R^3$, identically or differently, are H, halogen, substituted and/or unsubstituted alkyl $C_nH_{2n+1}$, substituted and/or unsubstituted alkenyl having 1–18 carbon atoms and one or more double bonds, substituted and/or unsubstituted alkynyl having 1–18 carbon atoms and one or more triple bonds, substituted and/or unsubstituted cycloalkyl $C_mH_{2m-1}$, mono- or polysubstituted and/or unsubstituted phenyl, substituted and/or unsubstituted heteroaryl,
A can be included in various positions in $R^1$, $R^2$ and/or $R_3$,
Kt can be included in cyclic or heterocyclic rings,
the groups bound to Kt can be identical or different,
where
n=1–18
M=3–7
k=0, 1–6
l=1 or 2 in the case of x=1 and 1 in the case x=0
x=0, 1 y=1–4.

The method of preparing these compounds is characterized in that an alkali metal salt of the general formula $$D^+ \ ^-N(CF_3)_2 \tag{II}$$

$D^+$ being selected from the group of the alkali metals, is reacted in a polar organic solvent with a salt of the general formula $$[([R^1(CR^2R^3)_k]_lA_x)_yKt]^+ \ ^-E \tag{III}$$

where

Kt, A, $R^1$, $R^2$, $R^3$, k, l, x and y have the abovementioned meanings and $^-E$ is $F^-$, $Cl^-$, $Br^-$, $I^-$, $BF_4^-$, $ClO_4^-$, $AsF_6^-$, $SbF_6^-$ or $PF_6^-$.

It is equally possible, however, to employ electrolytes comprising compounds of the general formula (DE 199 53 638)

$$X—(CYZ)_m—SO_2N(CR^1R^2R^3)_2$$

where

X is H, F, Cl, $C_nF_{2n+1}$, $C_nF_{2n-1}$, $(SO_2)_kN(CR^1R^2R^3)_2$

Y is H, F, Cl

Z is H, F, Cl $R^1$, $R^2$, $R^3$ are H and/or alkyl, fluoroalkyl, cycloalkyl m is 0–9 and if X=H, m≠0 n is 1–9 k is 0, if m=0, and k=1 if m=1–9, prepared by reacting partially fluorinated or per-fluorinated alkylsulfonyl fluorides with dimethylamine in organic solvents and complex salts of the general formula (DE 199 51 804)

$$M^{x+}[EZ]_{k/y}{}^{y-}$$

where x, y are 1, 2, 3, 4, 5, 6

$M^{x+}$ is a metal ion

E is a Lewis acid selected from the group $BR^1R^2R^3$, $AlR^1R^2R^3$, $PR^1R^2R^3R^4R^5$, $AsR^1R^2R^3R^4R^5$, $VR^1R^2R^3R^4R^5$, $R^1$ to $R^5$ are identical or different and are directly linked or are not directly linked to one another via a single or double bond, each, individually or jointly, have the meaning:

of a halogen (F, Cl, Br), of an alkyl or alkoxy radical ($C_1$ to $C_8$) which may be partially or completely substituted by F, Cl, Br, of an aromatic ring which is bound or not bound via oxygen, is selected from the group phenyl, naphthyl, anthracenyl or phenanthrenyl, and can be unsubstituted or mono- to hexasubstituted by alkyl ($C_1$ to $C_8$) or F, Cl, Br, of an aromatic heterocyclic ring which is bound or not bound via oxygen, is selected from the group pyridyl, pyrazyl or pyrimidyl, and can be unsubstituted or mono- to tetrasubstituted by alkyl ($C_1$ to $C_8$) or F, Cl, Br, and Z is $OR^6$, $NR^6R^7$, $CR^6R^7R^8$, $OSO_2R^6$, $N(SO_2R^6)$ $(SO_2R^7)$, $C(SO_2R^6)(SO_2R^7)(SO_2R^8)$, $OCOR^6$, where $R^6$ to $R^8$ are identical or different, are directly linked or not directly linked to one another via a single or double bond, and each, individually or jointly, have the meaning of a hydrogen or the meaning as $R^1$ to $R^5$, prepared by reacting an appropriate boron or phosphorus Lewis acid solvent adduct with a lithium or tetraalkylammonium imide, methanide or triflate.

Also present can be borate salts (DE 199 59 722) of the general formula

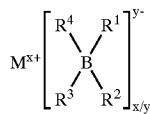

where

M is a metal ion or tetraalkylammonium ion, x, y are 1, 2, 3, 4, 5 or 6, $R^1$ to $R^4$ are identical or different alkoxy or carboxy radicals ($C_1$ to $C_8$) which are directly linked or are not directly linked to one another via a single or double bond. These borate salts are prepared by reacting lithium tetralcoholate borate or a 1:1 mixture of lithium alcoholate with a boric acid ester in an aprotic solvent with a suitable hydroxyl or carboxyl compound in a ratio of 2:1 or 4:1.

The additives can also be employed in electrolytes which comprise lithium fluoroalkyl phosphates of the general formula (I), $$Li^+[PF_x(C_yF_{2y+1-z}H_z)_{6-x}]^- \tag{I}$$

where $1 \leq x \leq 5$ $3 \leq y \leq 8$ $0 \leq z \leq 2y+1$ and the ligands ($C_yF_{2y+1-z}H_z$) can be identical or different, with the exception of the compounds of the general formula (I'), $$Li^+[PF_a(CH_bF_c(CF_3)_d)^e]^- \tag{I'}$$

in which a is an integer from 2 to 5, b=0 or 1, c=0 or 1, d=2 and e is an integer from 1 to 4, with the conditions that b and c are not simultaneously=0 and the sum a+e equals 6 and the ligands $(CH_bF_c(CF_3)_d)$ are identical or different (DE 100 089 55). The method for preparing lithium fluoroalkyl phosphates of the general formula (I) is characterized in that at least one compound of the general formula $$H_mP(C_nH_{2n+1})_{3-m} \tag{III}$$

$$OP(C_nH_{2n+1})_3 \tag{IV}$$

$$Cl_mP(C_nH_{2n+1})_{3-m} \tag{V}$$

$$F_mP(C_nH_{2n+1})_{3-m} \tag{VI}$$

$$Cl_oP(C_nH_{2n+1})_{5-o} \tag{VII}$$

$$F_oP(C_nH_{2n+1})_{5-o} \tag{VIII}$$

in each of which $0 \leq m \leq 2$, $3 \leq n \leq 8$ and $0 \leq o \leq 4$, is fluorinated by electrolysis in hydrogen fluoride, the fluorination product mixture thus obtained is separated by extraction, phase separation and/or distillation, and the fluorinated alkylphosphorane thus obtained is reacted with lithium fluoride in an aprotic solvent or solvent mixture with the exclusion of moisture, and the salt thus obtained of the general formula (I) is purified and isolated in accordance with standard procedures.

The additives can be employed in electrolytes for electrochemical cells which comprise anode material consisting of coated metal cores selected from the group Sb, Bi, Cd, In, Pb, Ga and tin or alloys of these (DE 100 16 024). The method for preparing said anode material is characterized in that a) a suspension of a sol of the metal core or alloy core is prepared in urotropine, b) the suspension is emulsified with $C_5$–$C_{12}$ hydrocarbons, c) the emulsion is precipitated onto the metal cores or alloy cores, and d) the metal hydroxides or oxihydroxides are converted into the corresponding oxide by annealing the system.

The additives can also be used in electrolytes for electrochemical cells comprising cathodes of standard lithium intercalation and insertion compounds, but alternatively comprising cathode materials which consist of lithium mixed oxide particles which are coated with one or more metal oxides (DE 199 22 522), by suspending the particles in an organic solvent, admixing the suspension with a solution of a hydrolysable metal compound and a hydrolysis solution and then filtering off the coated particles, drying them and calcining them if required. Alternatively, they can consist of lithium mixed oxide particles which are coated with one or more polymers (DE 199 46 066), obtained by a method in which the particles are suspended in a solvent and the coated particles are then filtered off, dried and calcined if required. Equally, the additives according to the invention can be used in systems comprising cathodes which consist of lithium mixed oxide particles, which are singly or multiply coated with alkali metal compounds and metal oxides (DE 100 14 884). The method for preparing these materials is characterized in that the particles are suspended in an organic solvent, an alkali metal salt compound suspended in an organic solvent is added, metal oxides dissolved in an organic solvent are added, the suspension is admixed with a hydrolysis solution, and the coated particles are then filtered off, dried and calcined.

A general example of the invention is explained below in more detail.

Preparation of the intermediate (II):

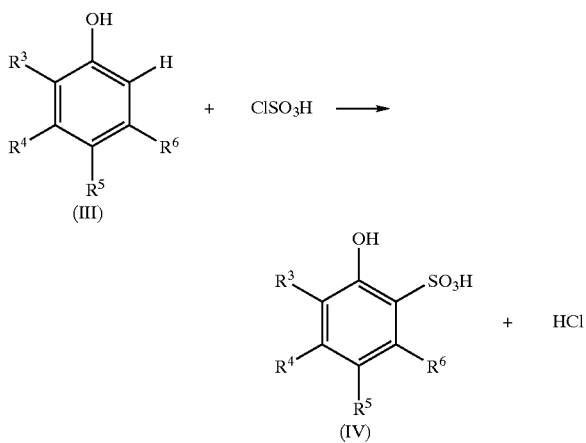

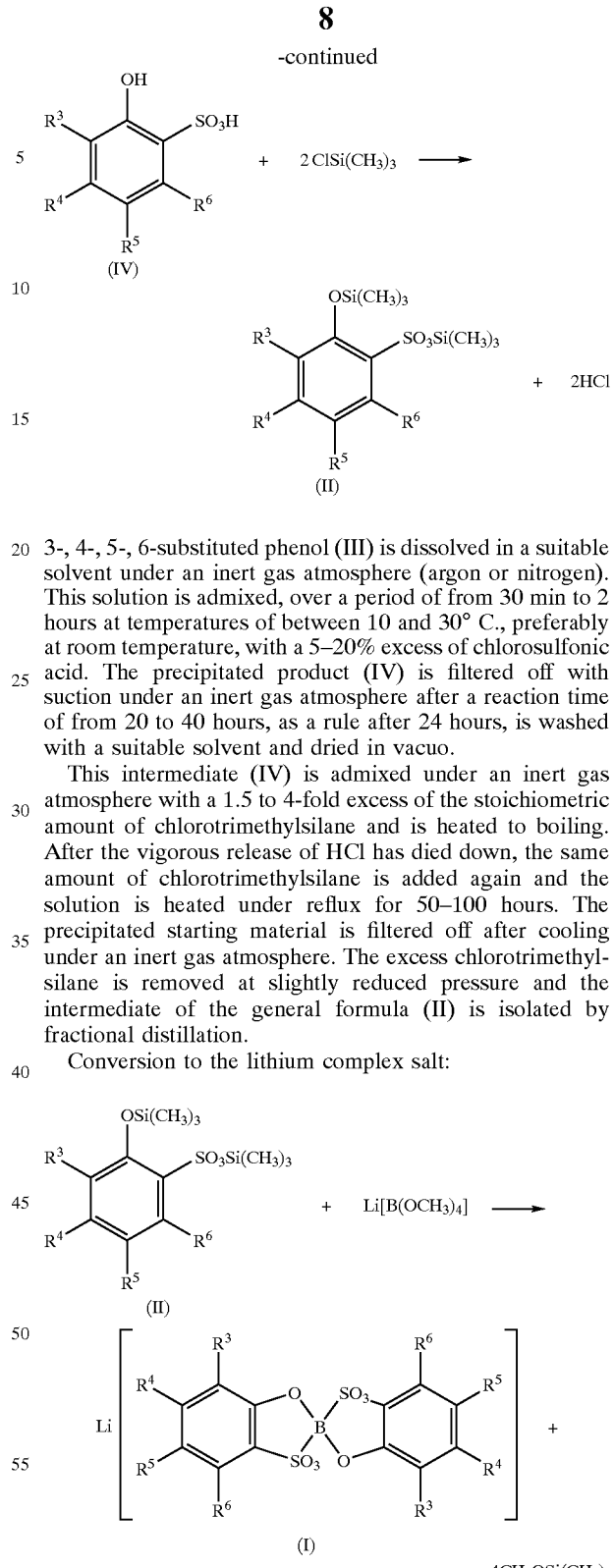

3-, 4-, 5-, 6-substituted phenol (III) is dissolved in a suitable solvent under an inert gas atmosphere (argon or nitrogen). This solution is admixed, over a period of from 30 min to 2 hours at temperatures of between 10 and 30° C., preferably at room temperature, with a 5–20% excess of chlorosulfonic acid. The precipitated product (IV) is filtered off with suction under an inert gas atmosphere after a reaction time of from 20 to 40 hours, as a rule after 24 hours, is washed with a suitable solvent and dried in vacuo.

This intermediate (IV) is admixed under an inert gas atmosphere with a 1.5 to 4-fold excess of the stoichiometric amount of chlorotrimethylsilane and is heated to boiling. After the vigorous release of HCl has died down, the same amount of chlorotrimethylsilane is added again and the solution is heated under reflux for 50–100 hours. The precipitated starting material is filtered off after cooling under an inert gas atmosphere. The excess chlorotrimethylsilane is removed at slightly reduced pressure and the intermediate of the general formula (II) is isolated by fractional distillation.

Conversion to the lithium complex salt:

To prepare the lithium complex salt (I), lithium tetraalcoholatoborate is introduced as initial charge in a polar aprotic solvent under an inert gas atmosphere. The solvent used can be a solvent from the group acetonitrile, acetone, nitromethane, dimethyl-formamide, dimethylacetamide, dimethyl sulfoxide, dimethyl carbonate, diethyl carbonate, propylene carbonate, butylene carbonate and methyl ethyl carbonate. After the addition of stoichiometric amounts of the intermediate (II) the mixture is stirred for from about half an hour to about 5 hours, preferably from about 45 min to about 90 min, at temperatures of between about 40 and about 70° C. The silane formed and the solvent are removed under slightly reduced pressure and the crude product is dried to constant weight in vacuo. The crude product is recrystallized from a suitable solvent or solvent mixture and then dried to constant weight in vacuo.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosure of all applications, patents and publications, cited above, and of corresponding German application No. 199 32 317.8, filed Jul. 10, 1999 is hereby incorporated by reference.

EXAMPLES

Example 1

5-Fluoro-2-hydroxybenzenesulfonic Acid 200 g (1.78 mol) of 4-fluorophenol are dissolved under a nitrogen atmosphere in 1300 ml of $CHCl_3$ (distilled, dried over $CaCl_2$). Added dropwise to this solution, over a period of 1 hour at room temperature with stirring, are 131 ml (229 g=1.96 mol) of chloro-sulfonic acid, a vigorous release of HCl being observed initially, which dies down 30 min after completion and ceases entirely after a further 3 hours. After a reaction time of 24 hours, the precipitated product is filtered off with suction at room temperature under inert gas, washed twice with 200 ml of $CHCl_3$ each time, and dried in vacuo at 1333 Pa and room temperature for 3 hours.

The product is a greyish-white, highly hygroscopic powder.

Yield: 302 g (88%) Melting point: 110–114° C. (sealed capillary); $^1$H-NMR (250 MHz, [$D_6$] DMSO): δ=6.77 (dd, $^3J_{H3-H4}$=8.9 Hz, $^4J_{H3-F}$=4.6 Hz, 1H, H-3) 7.04 (dt, $^3J_{H4-H3}$= 8.9 Hz, $^4J_{H4-H6}$=3.3 Hz, $^3J_{H4-F}$=8.9 Hz, 1H, H-4), 7.16 (dd, $^3J_{H6-F}$=8.4 Hz, $^4J_{H6-H4}$32 3.3 Hz, 1H, H-6), 12.32 (br. s, 2H, OH, $SO_3H$); $^{13}$C-NMR (62.9 MHz, [$D_6$]DMSO): δ=113.46 (+, d, $^2J_{C-F}$=24.0 Hz, C-6), 118.47 (+, d, $^3J_{C-F}$=7.4 Hz, C-3), 118.53 (+, d, $^2J_{C-F}$=23.0 Hz, C-4) 131.79 ($C_{quart}$, d, $^3J_{C-F}$= 5.8 Hz, C-1), 150.22 ($C_{quart}$, d, $^4J_{C-F}$=1.8 Hz, C-2), 155.10 ($C_{quart}$, d, $^1J_{C-F}$=236.3 Hz, C-5) MS (70 eV, El), m/z (%): 194 (2) [M$^+$+2], 193 (3) [M$^+$+1], 192 (54) [M$^+$], 174 (44), 126 (23), 110 (65), 98 (15), 82 (100), 63 (16), 57 (20) $C_6H_5O_4FS$: obs. 191.9892 (correct HRMS).

Example 2

Trimethylsilyl 5-Fluoro-2-trimethylsilyloxy-benzene-sulfonate 302 g (1.57 mol) of 5-fluoro-2-hydroxybenzenesulfonic acid are admixed, under an inert gas atmosphere at room temperature with stirring, with 794 ml (683 g, 6.28 mol) of chlorotrimethylsilane, and the mixture is heated to boiling. After the vigorous release of HCl has died down, a further 794 ml of chlorotrimethylsilane are added and the turbid solution is heated under reflux for 96 hours. After cooling, the precipitate is filtered off under inert gas, the excess chlorotrimethylsilane is removed at 40–50° C. under slightly reduced pressure (about 4000 Pa) and the product is obtained by fractional distillation in vacuo.

The product is a colorless, viscous, readily hydrolysable liquid.

Yield: 496 g (93%); Boiling point: 93–96° C./1.333 Pa; $^1$H-NMR (250 MHz, $CDCl_3$): δ=0.32 (s, 9H, OTMS), 0.36 (s, 9H, OTMS), 6.87 (dd, $^3J_{H3-H4}$=9.0 Hz, $^4J_{H3-F}$=4.3 Hz, 1H, H-3), 7.16 (ddd, $^3J_{H4-H3}$32 9.0 Hz, $^4J_{H4-H6}$32 3.2 Hz, $^3J_{H4-F}$=7.6 Hz, 1H, H-4), 7.57 (dd, $^4J_{H6-H4}$=3.2 Hz, $^3J_{H6-F}$= 8.0 Hz, 1H, H-6) $^{13}$C-NMR (62.9 MHz, $CDCl_3$): δ=0.38 (+, OTMS), 0.43 (+, OTMS), 116.23 (+, d, $^2J_{C-F}$=26.4 Hz, C-6), 121.08 (+, d, $^2J_{C-F}$=23.0 Hz, C-4), 121.70 (+, d, $^3J_{C-F}$=7.4 Hz, C-3), 130.99 ($C_{quart}$, d, $^3J_{C-F}$=7.3 Hz, C-1), 149.82 ($C_{quart}$, d, $^4J_{C-F}$=2.6 Hz, C-2), 155.77 ($C_{quart}$, d, $^1J_{C-F}$=243.2 Hz, C-5); MS (70 eV, El), m/z (%): 336 (3) [M$^+$], 321 (33), 264 (43), 249 (60), 233 (96), 169 (39), 147 (59), 75 (100), 73 (76), 45 (18); $C_{12}H_{21}O_4FSSi_2$: obs. 336.0683 (correct HRMS).

| Elemental analysis: | % C | % H |
|---|---|---|
| calculated: | 42.82 | 6.29 |
| observed: | 42.57 | 6.30 |

Example 3

Lithium bis[5-Fluoro-2-olato-benzenesulfonato(2–) O,O']-borate(1–)

2.81 g (19.8 mmol) of lithium tetramethanolato-borate (1–) are suspended under inert gas in 100 ml of dimethyl carbonate (DMC). Addition of 13.35 g (39.7 mmol) of trimethylsilyl 5-fluoro-2-trimethylsilyloxy-benzenesulfonate results in a clear solution. This is kept at 45–50° C. for one hour, becoming slightly turbid in the process. The silane formed is stripped off together with the solvent at 50° C. under slightly reduced pressure, and the crude product obtained is dried for 24 hours at 70° C. in an oil pump vacuum. The crude product is recrystallized four times from toluene/DMC. Clouding observed during the first two purification steps is removed by filtration via a glass frit. The lithium salt is dried to constant weight in vacuo at from 1 to 10 Pa at a temperature of 70° C.

The product is obtained in the form of colorless acicular crystals.

$^1$H-NMR (250 MHz, [$D_6$] DMSO): δ=7.08 (dd, $^3J_{H3-H4}$= 8.9 Hz, $^4J_{H3-F}$=4.4 Hz, 2H, H-3, H-3'), 7.40 (dt, $^3J_{H4-H3}$=8.9 Hz, $^4J_{H4-H6}$=3.2 Hz, $^3J_{H4-F}$=8.9 Hz, 2H, H-4, H-4'), 7.50 (dd, $^4J_{H6-H4}$=3.2 Hz, $^3J_{H6-F}$=8.9 Hz, 2H, H-6, H-6'); $^{13}$C-NMR (62.9 MHz, [$D_6$DMSO]): δ=110.6 (+, d, $^2J_{C-F}$=25.7 Hz, C-6), 121.3 (+, d, $^2J_{C-F}$=22.9 Hz, C-4); 121.4 (+, d, $^3J_{C-F}$= 7.9 Hz, C-3); 125.3 ($C_{quart}$, $^3J_{C-F}$=7.6 Hz, C-1); 148.9 ($C_{quart}$, $^4J_{C-F}$=2.2 Hz, C-2); 155.2 ($C_{quart}$, $^1J_{C-F}$=240.0 Hz, C-5).

AAS: Lithium Content:

Calculated: 1.74% Observed: 1.75%.

Example 4

Oxidation Resistance of Lithium bis[5-Fluoro-2-olato-benzenesulfonato(2–)O,O']borate(1–)

A measuring cell comprising a platinum working electrode, lithium counterelectrode and lithium reference electrode was used to record, in each case, 5 cyclovoltammograms successively. To do this, the potential, starting from the rest potential, was first increased at a rate of 10 mV/s to 5 V against Li/Li$^+$ and subsequently run back to the rest potential.

Electrolyte: 0.42 mol/kg$_{Lm}$ lithium bis[5-fluoro-2-olato-benzenesulfonato(2−)O,O']borate(1−) EC/DMC (1:1)

The oxidation potential was measured as 4.5 V against Li/Li$^+$.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method of preparing a lithium complex salt of the formula (I)

$$\left[ \text{Li} \quad \begin{array}{c} R^6 \\ R^5 \\ R^4 \\ R^3 \end{array} \diagdown \text{ring with } SO_2\text{-O-B(OR}^1)(OR^2)\text{-O} \right] \quad (I)$$

where
R$^1$ and R$^2$ are optionally directly linked to one another via a single or double bond, and each, independently is phenyl, naphthyl, anthracenyl or phenanthrenyl, optionally mono- to hexasubstituted by C$_1$–C$_6$ alkyl, C$_1$–C$_6$-alkoxy or halogen;

or each independently is pyridyl, pyrazyl or pyrimidyl, each optionally mono- to tetrasubstituted by C$_1$–C$_6$-alkyl, C$_1$–C$_6$-alkoxy or halogen;

or each independently is hydroxybenzenecarboxyl, hydroxynaphthalenecarboxyl, hydroxybenzenesulfonyl or hydroxynaphthalenesulfonyl, each optionally mono- to tetrasubstituted by C$_1$–C$_6$ alkyl, C$_1$–C$_6$-alkoxy groups or halogen;

ring substituents R$^3$–R$^6$ are optionally directly linked to an adjacent ring substituent via a single or double bond and are C$_1$–C$_6$-alkyl, C$_1$–C$_6$-alkoxy or halogen, phenyl, naphthyl, anthracenyl or phenanthrenyl, each optionally mono- to hexasubstituted by C$_1$–C$_6$-alkyl, C$_1$–C$_6$-alkoxy or halogen; pyridyl, pyrazyl or pyrimidyl, each optionally mono- to tetrasubstituted by C$_1$–C$_6$-alkyl, C$_1$–C$_6$-alkoxy or halogen;

said method comprising:
a) admixing a 3-, 4-, 5-, 6-substituted phenol in a suitable solvent with chlorosulfonic acid to form a first intermediate;
b) reacting the first intermediate from a) with chlorotrimethylsilane to form a second intermediate; and
c) reacting the second intermediate from b) with lithium tetramethanolate borate (1−) in a suitable solvent to produce an end product of formula (I) therefrom.

2. The method according to claim 1, wherein the suitable solvent in c) is a polar aprotic solvent.

3. A method of preparing a compound of formula (I)

$$\left[ \text{Li} \quad \begin{array}{c} R^6 \\ R^5 \\ R^4 \\ R^3 \end{array} \diagdown \text{ring with } SO_2\text{-O-B(OR}^1)(OR^2)\text{-O} \right] \quad (I)$$

where
R$^1$ and R$^2$ are optionally directly linked to one another via a single or double bond,
and each, independently is phenyl, naphthyl, anthracenyl or phenanthrenyl, optionally mono- to hexasubstituted by C$_1$–C$_6$ alkyl, C$_1$–C$_6$-alkoxy or halogen, or each independently is pyridyl, pyrazyl or pyrimidyl, each optionally mono- to tetrasubstituted by C$_1$–C$_6$-alkyl, C$_1$–C$_6$-alkoxy or halogen;

or each independently is hydroxybenzenecarboxyl, hydroxynaphthalenecarboxyl, hydroxybenzenesulfonyl or hydroxynaphthalenesulfonyl, each optionally mono- to tetrasubstituted by C$_1$–C$_6$-alkyl, C$_1$–C$_6$-alkoxy or halogen;

ring substituents R$^3$–R$^6$ are optionally directly linked to an adjacent ring substituent via a single or double bond and are C$_1$–C$_6$-alkyl, C$_1$–C$_6$-alkoxy or halogen, phenyl, naphthyl, anthracenyl or phenanthrenyl, each optionally mono- to hexasubstituted by C$_1$–C$_6$-alkyl, C$_1$–C$_6$-alkoxy or halogen;

pyridyl, pyrazyl or pyrimidyl, each optionally mono- to tetrasubstituted by C$_1$–C$_6$-alkyl, C$_1$–C$_6$-alkoxy or halogen;

comprising:
reacting a compound of formula II $$\begin{array}{c} R^6 \\ R^5 \\ R^4 \\ R^3 \end{array} \diagdown \text{ring with } SO_3R^1 \text{ and } OR^2 \quad (II)$$

where R$^1$ and R$^2$ are each independently:
H, C$_1$–C$_6$-alkyl or C$_1$–C$_6$-trialkylsilyl,
ring substituents R$^3$–R$^6$ are optionally directly linked to an adjacent ring substituent via a single or double bond, and are C$_1$–C$_6$-alkyl, C$_1$–C$_6$-alkyloxy or halogen;

phenyl, naphthyl, anthracenyl or phenanthrenyl, each optionally mono- to hexasubstituted by C$_1$–C$_6$-alkyl, C$_1$–C$_6$-alkoxy groups or halogen;

pyridyl, pyrazyl or pyrimidyl, each optionally mono- to tetrasubstituted by C$_1$–C$_6$-alkyl, C$_1$–C$_6$-alkoxy groups or halogen;

with lithium tetramethylate borate.

4. The method according to claim 3, wherein the lithium tetramethodate borate is introduced in a polar aprotic solvent.

5. The method according to claim 4, wherein the polar aprotic solvent is acetonitrile, acetone, nitromethane, dimethyformamide, dimethylacetamide, dimethyl sulfoxide, dimethyl carbonate, propylene carbonate, butylene carbonate or methyl ethyl carbonate.

6. The method according to claim 4, wherein the reaction is between about 40° C. to about 70° C.

7. The method according to claim 4, wherein reactants are stirred for about 0.5 to about 5 hours.

8. The method of claim 1, further comprising filtering and subjecting the second intermediate to fractional distillation prior to reacting the second intermediate and isolating the end product.

9. The method according to claim 1, wherein the first intermediate compound is of the formula (IV):

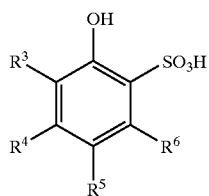

IV where the ring substituents $R^3$–$R^6$ are as defined in claim 1.

10. The method according to claim 1, wherein the second intermediate compound is of the formula (II):

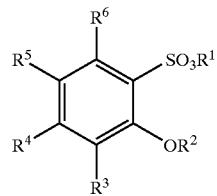

(II)

where $R_1$–$R^6$ are as defined in claim 1.

11. The method of claim 1, wherein the admixing is conducted in an atmosphere of argon or nitrogen.

12. The method of claim 1, wherein the admixing is conducted over a period of 0.5–2 hours at temperatures of 10° C.–30° C.

13. The method according to claim 1, wherein the first intermediate compound is 5-fluoro2-hydroxybenzenesulfonic acid.

14. The method according to claim 1, wherein the second intermediate compound is trimethylsilyl 5-fluoro-2-trimethylsilyloxy-benzenesulfonate.

* * * * *